US012668787B2

(12) United States Patent
Griswold et al.

(10) Patent No.: US 12,668,787 B2
(45) Date of Patent: *Jun. 30, 2026

(54) UNGLYCOSYLATED LYSOSTAPHIN VARIANT PROTEIN

(71) Applicant: Trustees of Dartmouth College, Hanover, NH (US)

(72) Inventors: Karl E. Griswold, Lyme, NH (US); Hongliang Zhao, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/746,808

(22) Filed: Jun. 18, 2024

(65) Prior Publication Data

US 2025/0059526 A1    Feb. 20, 2025

Related U.S. Application Data

(62) Division of application No. 17/480,166, filed on Sep. 21, 2021, now Pat. No. 12,049,653, which is a division of application No. 14/907,746, filed as application No. PCT/US2014/046786 on Jul. 16, 2014, now Pat. No. 11,155,801.

(60) Provisional application No. 61/862,599, filed on Aug. 6, 2013.

(51) Int. Cl.
*C12N 9/52* (2006.01)
*A61K 38/00* (2006.01)

(52) U.S. Cl.
CPC ........ *C12N 9/52* (2013.01); *C12Y 304/24075* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,931,390 | A | 6/1990 | Recsei |
| 6,897,041 | B1 | 5/2005 | Khatri et al. |
| 8,241,901 | B2 | 8/2012 | Huang et al. |
| 2002/0006406 | A1 | 1/2002 | Goldstein et al. |
| 2005/0118159 | A1 | 6/2005 | Stinson et al. |
| 2006/0216782 | A1 | 9/2006 | Neville et al. |
| 2008/0095756 | A1 | 4/2008 | Stinson et al. |
| 2009/0186380 | A1 | 7/2009 | Huang et al. |

FOREIGN PATENT DOCUMENTS

| | | |
|---|---|---|
| EP | 0 299 978 B1 | 8/1993 |
| EP | 1 224 271 B1 | 5/2009 |
| KR | 1020027004972 | 8/2002 |
| WO | WO 2001/029201 A1 | 4/2001 |
| WO | WO 2003/082184 A2 | 10/2003 |
| WO | WO 2007/009351 A1 | 1/2007 |

OTHER PUBLICATIONS

Bahrampour et al., "Alteration in protein profile of *Pseudomonas aeruginosa* (PTSOX4) coated with magnetic $Fe_3O_4$ nanoparticles", *Journal of Nanostructure in Chemistry* 3:58 (2013).

Bai et al., "A Gene Optimization Strategy that Enhances Production of Fully Functional P-Glycoprotein in *Pichia pastoris*", PLOS ONE 6(8):e22577 (2011).

Cregg et al., "Expression in the Yeast *Pichia pastoris*", *Methods of Enzymology* 463:169-189 (2009).

Defres et al., "MRSA as a cause of lung infection including airway infection, community-acquired pneumonia and hospital-acquired pneumonia", *European Respiratory Journal* 34(6):1470-1476 (2009).

Depourcq et al., "Engineering the yeast *Yarrowia lipolytica* for the production of therapeutic proteins homogeneously glycosylated with $Man_8GlcNAc_2$ and $Man_5GlcNAc_2$", *Microbial Cell Factories* 11:53 (2012).

Fowler et al., "*Staphylococcus aureus* Endocarditis: A Consequence of Medical Progress", *JAMA* 293(24):3012-3021 (2005).

Gargis et al., "Complete nucleotide sequences of plasmids pACK1 and PACK3 from *Staphylococcus simulans* biovar staphylolyticus", *Plasmid* 64(2):104-109 (2010).

Gasser et al., "*Pichia pastoris*: protein production host and model organism for biomedical research", *Future Microbiology* 8(2):191-208 (2013).

Grundmann et al., "Emergence and resurgence of meticillin-resistant *Staphylococcus aureus* as a public-health threat", *The Lancet* 368:874-885 (2006).

Gurramkonda et al., "Simple high-cell density fed-batch technique for high-level recombinant protein production with *Pichia pastoris*: Application to intracellular production of Hepatitis B surface antigen", *Microbial Cell Factories* 8:13 (2009).

Harris et al., "Effect of Lysostaphin on Staphylococcal Carriage in Infants and Children", *Antimicrobial Agents and Chemotherapy* 7:110-112 (1967).

Harrison et al., "Antigenic Response to Topically Applied Proteins", *Infection and Immunity* 11(2):309-312 (1975).

Henderson et al., "Occurrence of the human tumor-specific antigen structure Galß1-3GalNAcα-(Thomsen-Friedenreich) and related structures on gut bacteria: Prevalence, immunochemical analysis and structural confirmation", *Glycobiology* 21(10):1277-1289 (2011).

(Continued)

*Primary Examiner* — Louise W Humphrey
*Assistant Examiner* — Sharon M. Papciak
(74) *Attorney, Agent, or Firm* — Saul Ewing LLP; Domingos J. Silva; Justin Crotty

(57) ABSTRACT

Unglycosylated lysostaphin variant protein, nucleic acid molecule, vector and host cell, as well as a method for production of unglycosylated lysostaphin variant protein in a yeast expression system are provided. The proteins are produced in a *Pichia pastoris* expression system and have been shown to have activity equivalent to wild-type lysostaphin. The lysostaphin variant proteins can be used as therapeutic proteins for treatment of diseases such as *Staphylococcus aureus* infection.

9 Claims, 2 Drawing Sheets

Specification includes a Sequence Listing.

(56)                    References Cited

OTHER PUBLICATIONS

Hospital Infections Program "National Nosocomial Infections Surveillance (NNIS) System Report, Data Summary from Jan. 1990-May 1999, issued Jun. 1999. A report from the NNIS System", *American Journal of Infection Control* 27:520-532 (1999).

Huang et al., "Site-specific N-glycosylation of caprine lysostaphin restricts its bacteriolytic activity toward *Staphylococcus aureus*", *Animal Biotechnology* 24:129-147 (2013).

International Preliminary Report on Patentability in PCT/US14/46786 mailed Feb. 9, 2016.

International Search Report and Written Opinion in PCT/US14/46786 mailed Jan. 30, 2015.

Kokai-Kun et al., "Lysostaphin eradicates established *Staphylococcus aureus* biofilms in jugular vein catheterized mice", *Journal of Antimicrobial Chemotherapy* 64:94-100 (2009).

Lowy, "Secrets of a superbug", *Nature Medicine* 13(12):1418-1420 (2007).

Martin et al., "The reacquisition of staphylococci by treated carriers: A demonstration of bacterial interference", *The Journal of Laboratory and Clinical Medicine* 71(5):791-797 (1968).

Mierau et al., "Industrial-scale production and purification of a heterologous protein in *Lactococcus lactis* using the nisin-controlled gene expression system NICE: The case of lysostaphin", *Microbial Cell Factories* 4:15 (2005).

Mierau et al., "Optimization of the *Lactococcus lactis* nisin-controlled gene expression system NICE for industrial applications", *Microbial Cell Factories* 4:16 (2005).

Pantosti et al., "What is MRSA?" *European Respiratory Journal* 34:1190-1196 (2009).

Quickel et al., "Efficacy and Safety of Topical Lysostaphin Treatment of Persistent Nasal Carriage of *Staphylococcus aureus*", *Applied Microbiology* 22(3):446-450 (1971).

Recsei et al., "Cloning, sequence, and expression of the lysostaphin gene from *Staphylococcus simulans*", *PNAS USA* 84:1127-1131 (1987).

Schindler et al., "Lysostaphin: A New Bacteriolytic Agent for the *Staphylococcus*", *PNAS USA* 51:414-421 (1964).

Science Buddies. A/T content. Datasheet [online]. [retrieved on Jun. 13, 2017]. Copyright 2002-2017. Science Buddies. Retrieved from the Internet: <URL: http://www.sciencebuddies.org/science-fair-projects/project_ideas/Genom_GC_Calculator.shtml>.

Sharma et al., "Cytoplasmic expression of mature glycylglycine endopeptidase lysostaphin with an amino terminal hexa-histidine in a soluble and catalytically active form in *Escherichia coli*", *Protein Expression and Purification* 45:206-215 (2006).

Stark et al., "Systemic lysostaphin in man-apparent antimicrobial activity in a neutropenic patient", *The New England Journal of Medicine* 291(5):239-240 (1974).

Szweda et al., "Cloning, Expression, and Purification of the *Staphylococcus simulans* Lysostaphin Using the Intein-Chitin-Binding Domain (CBD) System", *Protein Expression and Purification* 22:467-471 (2001).

Szweda et al., "New effective sources of the *Staphylococcus simulans* lysostaphin", *Journal of Biotechnology* 117:203-213 (2005).

Szweda et al., "Peptidoglycan hydrolases-potential weapons against *Staphylococcus aureus*", *Applied Microbiology and Biotechnology* 96:1157-1174 (2012).

Taubes, "The Bacteria Fight Back", *Science* 321:356-361 (2008).

Vogl et al., "New opportunities by synthetic biology for biopharmaceutical production in *Pichia pastoris*", *Current Opinion in Biotechnology* 24(6):1094-1101 (2013); doi:pii:S0958-1669(13)00038-4.10.1016/j.copbio. 2013.02.024.

Walsh et al., "Improved Pharmacokinetics and Reduced Antibody Reactivity of Lysostaphin Conjugated to Polyethylene Glycol", *Antimicrobial Agents and Chemotherapy* 47(2):554-558 (2003).

Williamson et al., "Expression of the Lysostaphin Gene of *Staphylococcus simulans* in a Eukaryotic System", *Applied and Environmental Microbiology* 60(3):771-776 (1994).

Winnard et al., "Teleost introns are characterized by a high A+T content", *Comparative Biochemistry and Physiology Part B* 133:155-161 (2002).

Wisplinghoff et al., "Nosocomial Bloodstream Infections in US Hospitals: Analysis of 24,179 Cases from a Prospective Nationwide Surveillance Study", *Clinical Infectious Diseases* 39:309-317 (2004).

Wu et al., "Lower Temperature Cultures Enlarge the Effects of *Vitreoscilla* Hemoglobin Expression on Recombinant *Pichia pastoris*", *International Journal of Molecular Sciences* 13:13212-13226 (2012).

Yang et al., "de novo Design and Synthesis of *Candida Antarctica* Lipase B Gene and α-Factor Leads to High-Level Expression in *Pichia pastoris*", *PLOS ONE* 8(1):e53939 (2013); doi:10,137/journal.pone.0053939.

Zhao et al., "Gene and Protein Sequence Optimization for High-Level Production of Fully Active and Aglycosylated Lysostaphin in *Pichia pastoris*", *Applied and Environmental Microbiology* 80(9):2746-2753 (2014); doi:10.1128/AEM.03914-13.

Zhdaova et al., "Cloning of lysozyme and lysostaphin genes of Staphylococcus aureus and their expression in Bacillus subtilis cells", *Journal of Microbiology Epidemiology and Immunobiology* 4:3-6 (2001) (with English Abstract).

Zygmunt et al., "Lysostaphin: Model for a Specific Enzymatic Approach to Infectious Disease", *Progress in Drug Research* 16:309-333 (1972).

U.S. Appl. No. 17/480,166, filed Sep. 21, 2021, US 2022-0213460 A1, Jul. 7, 2022, U.S. Pat. No. 12,049,653, Jul. 30, 2024, Karl E. Griswold.

SEQUENCE LISTING

Sequence total quantity: 52
SEQ ID NO: 1          moltype = AA  length = 246
FEATURE               Location/Qualifiers
source                1..246

```
                              mol_type = protein
                              organism = Staphylococcus simulans
SEQUENCE: 1
AATHEHSAQW LNNYKKGYGY GPYPLGINGG MHYGVDFFMN IGTPVKAISS GKIVEAGWSN      60
YGGGNQIGLI ENDGVHRQWY MHLSKYNVKV GDYVKAGQII GWSGSTGYST APHLHFQRMV     120
NSFSNSTAQD PMPFLKSAGY GKAGGTVTPT PNTGWKTNKY GTLYKSESAS FTPNTDIITR     180
TTGPFRSMPQ SGVLKAGQTI HYDEVMKQDG HVWVGYTGNS GQRIYLPVRT WNKSTNTLGV     240
LWGTIK                                                                246

SEQ ID NO: 2              moltype = DNA  length = 741
FEATURE                   Location/Qualifiers
source                    1..741
                          mol_type = other DNA
                          organism = Staphylococcus simulans
SEQUENCE: 2
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca aagaatggtt     360
aattcatttt caaattcaac tgcccaagat ccaatgcctt tcttaaagag cgcaggatat     420
ggaaaagcag gtggtacagt aactccaacg cccaatacag gttggaaaac aaacaaatat     480
ggcacactat ataaatcaga gtcagctagc ttcacaccta atacagatat aataacaaga     540
acgactggtc catttagaag catgccgcag tcaggagtct aaaagcagg tcaaacaatt     600
cattatgatg aagtgatgaa acaagacggt catgtttggg taggttatac aggtaacagt     660
ggccaacgta tttacttgcc tgtaagaaca tggaataaat ctactaatac tttaggtgtt     720
ctttgggga ctataaagtg a                                                741

SEQ ID NO: 3              moltype = DNA  length = 741
FEATURE                   Location/Qualifiers
misc_feature             1..741
                          note = Synthetic polynucleotide
source                    1..741
                          mol_type = other DNA
                          organism = synthetic construct
SEQUENCE: 3
gctgctaccc acgagcactc cgctcaatgg ttgaacaact acaagaaggg ttacggttac      60
ggtccatacc cattgggtat caacggtggt atgcactacg gtgttgactt cttcatgaac     120
atcggtaccc cagtcaaggc tatctcctcc ggtaagatcg tcgaggctgg ttggtccaac     180
tacggtggtg gtaaccaaat cggtttgatc gagaacgacg gtgtccacag acaatggtac     240
atgcacttgt ccaagtacaa cgtcaaggtc ggtgactacg tcaaggctgg tcaaatcatc     300
ggttggtccg gttccaccgg ttactccacc gctccacact tgcacttcca aagaatggtc     360
aactccttct ccaactccac cgctcaagac ccaatgccat tcttgaagtc cgctggttac     420
ggtaaggctg gtggtaccgt caccccaacc ccaaacaccg gttggaagac caacaagtac     480
ggtaccttgt acaagtccga gtccgcttcc ttcaccccaa acaccgacat catcaccaga     540
accaccggtc cattcagatc catgccacaa tccggtgtct tgaaggctgg tcaaaccatc     600
cactacgacg aggtcatgaa gcaagacggt cacgtctggg tcggttacac cggtaactcc     660
ggtcaaagaa tctacttgcc agtcagaacc tggaacaagt ccaccaacac cttgggtgtc     720
ttgtgggta ccatcaagta a                                                741

SEQ ID NO: 4              moltype = AA  length = 246
FEATURE                   Location/Qualifiers
REGION                    1..246
                          note = Synthetic polypeptide
source                    1..246
                          mol_type = protein
                          organism = synthetic construct
SEQUENCE: 4
AATHEHSAQW LNNYKKGYGY GPYPLGINGG MHYGVDFFMN IGTPVKAISS GKIVEAGWSN      60
YGGGNQIGLI ENDGVHRQWY MHLSKYNVKV GDYVKAGQII GWSGSTGYST APHLHFQRMV     120
NSFSNPTAQD PMPFLKSAGY GKAGGTVTPT PNTGWKTNKY GTLYKSESAS FTPNTDIITR     180
TTGPFRSMPQ SGVLKAGQTI HYDEVMKQDG HVWVGYTGNS GQRIYLPVRT WNKSTNTLGV     240
LWGTIK                                                                246

SEQ ID NO: 5              moltype = DNA  length = 741
FEATURE                   Location/Qualifiers
misc_feature             1..741
                          note = Synthetic polynucleotide
source                    1..741
                          mol_type = other DNA
                          organism = synthetic construct
SEQUENCE: 5
gctgctaccc acgagcactc cgctcaatgg ttgaacaact acaagaaggg ttacggttac      60
ggtccatacc cattgggtat caacggtggt atgcactacg gtgttgactt cttcatgaac     120
atcggtaccc cagtcaaggc tatctcctcc ggtaagatcg tcgaggctgg ttggtccaac     180
tacggtggtg gtaaccaaat cggtttgatc gagaacgacg gtgtccacag acaatggtac     240
atgcacttgt ccaagtacaa cgtcaaggtc ggtgactacg tcaaggctgg tcaaatcatc     300
ggttggtccg gttccaccgg ttactccacc gctccacact tgcacttcca aagaatggtc     360
```

-continued

```
aactccttct ccaacccaac cgctcaagac ccaatgccat tcttgaagtc cgctggttac   420
ggtaaggctg gtggtaccgt caccccaacc ccaaacaccg gttggaagac caacaagtac   480
ggtaccttgt acaagtccga gtccgcttcc ttcaccccaa acaccgacat catcaccaga   540
accaccggtc cattcagatc catgccacaa tccggtgtct tgaaggctgg tcaaaccatc   600
cactacgacg aggtcatgaa gcaagacggt cacgtctggg tcggttacac cggtaactcc   660
ggtcaaagaa tctacttgcc agtcagaacc tggaacaagt ccaccaacac cttgggtgtc   720
ttgtggggta ccatcaagta a                                            741

SEQ ID NO: 6             moltype = AA   length = 246
FEATURE                  Location/Qualifiers
REGION                   1..246
                         note = Synthetic polypeptide
source                   1..246
                         mol_type = protein
                         organism = synthetic construct
SEQUENCE: 6
AATHEHSAQW LNNYKKGYGY GPYPLGINGG MHYGVDFFMN IGTPVKAISS GKIVEAGWSN   60
YGGGNQIGLI ENDGVHRQWY MHLSKYNVKV GDYVKAGQII GWSGSTGYST APHLHFQRMV   120
NSFSNSAAQD PMPFLKSAGY GKAGGTVTPT PNTGWKTNKY GTLYKSESAS FTPNTDIITR   180
TTGPFRSMPQ SGVLKAGQTI HYDEVMKQDG HVWVGYTGNS GQRIYLPVRT WNKSTNTLGV   240
LWGTIK                                                             246

SEQ ID NO: 7             moltype = DNA   length = 741
FEATURE                  Location/Qualifiers
misc_feature             1..741
                         note = Synthetic polynucleotide
source                   1..741
                         mol_type = other DNA
                         organism = synthetic construct
SEQUENCE: 7
gctgctaccc acgagcactc cgctcaatgg ttgaacaact acaagaaggg ttacggttac   60
ggtccatacc cattgggtat caacggtggt atgcactacg gtgttgactt cttcatgaac   120
atcggtaccc cagtcaaggc tatctcctcc ggtaagatcg tcgaggctgg ttggtccaac   180
tacggtggtg gtaaccaaat cggtttgatc gagaacgacg gtgtccacag acaatggtac   240
atgcacttgt ccaagtacaa cgtcaaggtc ggtgactacg tcaaggctgg tcaaatcatc   300
ggttggtccg gttccaccgg ttactccacc gctccacact tgcacttcca aagaatggtc   360
aactccttct ccaactccgc tgctcaagac ccaatgccat tcttgaagtc cgctggttac   420
ggtaaggctg gtggtaccgt caccccaacc ccaaacaccg gttggaagac caacaagtac   480
ggtaccttgt acaagtccga gtccgcttcc ttcaccccaa acaccgacat catcaccaga   540
accaccggtc cattcagatc catgccacaa tccggtgtct tgaaggctgg tcaaaccatc   600
cactacgacg aggtcatgaa gcaagacggt cacgtctggg tcggttacac cggtaactcc   660
ggtcaaagaa tctacttgcc agtcagaacc tggaacaagt ccaccaacac cttgggtgtc   720
ttgtggggta ccatcaagta a                                            741

SEQ ID NO: 8             moltype = AA   length = 246
FEATURE                  Location/Qualifiers
REGION                   1..246
                         note = Synthetic polypeptide
source                   1..246
                         mol_type = protein
                         organism = synthetic construct
SEQUENCE: 8
AATHEHSAQW LNNYKKGYGY GPYPLGINGG MHYGVDFFMN IGTPVKAISS GKIVEAGWSN   60
YGGGNQIGLI ENDGVHRQWY MHLSKYNVKV GDYVKAGQII GWSGSTGYST APHLHFQRMV   120
NSFSNSTAQD PMPFLKSAGY GKAGGTVTPT PNTGWKTNKY GTLYKSESAS FTPNTDIITR   180
TTGPFRSMPQ SGVLKAGQTI HYDEVMKQDG HVWVGYTGNS GQRIYLPVRT WNKSTNTLGV   240
LWGTIK                                                             246

SEQ ID NO: 9             moltype = DNA   length = 15
FEATURE                  Location/Qualifiers
source                   1..15
                         mol_type = other DNA
                         organism = Staphylococcus simulans
SEQUENCE: 9
aataattaca aaaa                                                     15

SEQ ID NO: 10            moltype = DNA   length = 17
FEATURE                  Location/Qualifiers
source                   1..17
                         mol_type = other DNA
                         organism = Staphylococcus simulans
SEQUENCE: 10
attttttat gaatatt                                                   17

SEQ ID NO: 11            moltype = DNA   length = 16
FEATURE                  Location/Qualifiers
source                   1..16
                         mol_type = other DNA
                         organism = Staphylococcus simulans
```

-continued

```
SEQUENCE: 11
taaatataat gttaaa                                                   16

SEQ ID NO: 12         moltype = DNA   length = 49
FEATURE               Location/Qualifiers
source                1..49
                      mol_type = other DNA
                      organism = Staphylococcus simulans
SEQUENCE: 12
tagacaatgg tatatgcatc taagtaaata taatgttaaa gtaggagat              49

SEQ ID NO: 13         moltype = DNA   length = 49
FEATURE               Location/Qualifiers
misc_feature          1..49
                      note = Synthetic polynucleotide
source                1..49
                      mol_type = other DNA
                      organism = synthetic construct
SEQUENCE: 13
cagacaatgg tacatgcact tgtccaagta caacgtcaag gtcggtgac              49

SEQ ID NO: 14         moltype = DNA   length = 49
FEATURE               Location/Qualifiers
misc_feature          1..49
                      note = Synthetic polynucleotide
source                1..49
                      mol_type = other DNA
                      organism = synthetic construct
SEQUENCE: 14
cagacaatgg tacatgcact tgtctaaata taatgttaaa gtcggtgac              49

SEQ ID NO: 15         moltype = DNA   length = 49
FEATURE               Location/Qualifiers
misc_feature          1..49
                      note = Synthetic polynucleotide
source                1..49
                      mol_type = other DNA
                      organism = synthetic construct
SEQUENCE: 15
tagacaatgg tatatgcatc taagcaagta caacgtcaag gtaggagat              49

SEQ ID NO: 16         moltype = DNA   length = 28
FEATURE               Location/Qualifiers
misc_feature          1..28
                      note = Synthetic oligonucleotide
source                1..28
                      mol_type = other DNA
                      organism = synthetic construct
SEQUENCE: 16
atcgctcgag aaaagagctg caacacat                                     28

SEQ ID NO: 17         moltype = DNA   length = 28
FEATURE               Location/Qualifiers
misc_feature          1..28
                      note = Synthetic oligonucleotide
source                1..28
                      mol_type = other DNA
                      organism = synthetic construct
SEQUENCE: 17
cgatgaattc ttactttata gttcccca                                     28

SEQ ID NO: 18         moltype = DNA   length = 28
FEATURE               Location/Qualifiers
misc_feature          1..28
                      note = Synthetic oligonucleotide
source                1..28
                      mol_type = other DNA
                      organism = synthetic construct
SEQUENCE: 18
atcgctcgag aaaagagctg ctacccac                                     28

SEQ ID NO: 19         moltype = DNA   length = 28
FEATURE               Location/Qualifiers
misc_feature          1..28
                      note = Synthetic oligonucleotide
source                1..28
                      mol_type = other DNA
                      organism = synthetic construct
SEQUENCE: 19
```

-continued

```
cgatgaattc ttacttgatg gtacccca                                                   28

SEQ ID NO: 20              moltype = DNA   length = 42
FEATURE                    Location/Qualifiers
misc_feature               1..42
                           note = Synthetic oligonucleotide
source                     1..42
                           mol_type = other DNA
                           organism = synthetic construct
SEQUENCE: 20
caaagaatgg ttaattcatt ttcccaatcc accgctcaag ac                                   42

SEQ ID NO: 21              moltype = DNA   length = 42
FEATURE                    Location/Qualifiers
misc_feature               1..42
                           note = Synthetic oligonucleotide
source                     1..42
                           mol_type = other DNA
                           organism = synthetic construct
SEQUENCE: 21
gtcttgagcg gtggattggg aaaatgaatt aaccattctt tg                                   42

SEQ ID NO: 22              moltype = DNA   length = 42
FEATURE                    Location/Qualifiers
misc_feature               1..42
                           note = Synthetic oligonucleotide
source                     1..42
                           mol_type = other DNA
                           organism = synthetic construct
SEQUENCE: 22
caaagaatgg tcaactcctt ctcaaattca actgcccaag at                                   42

SEQ ID NO: 23              moltype = DNA   length = 42
FEATURE                    Location/Qualifiers
misc_feature               1..42
                           note = Synthetic oligonucleotide
source                     1..42
                           mol_type = other DNA
                           organism = synthetic construct
SEQUENCE: 23
atcttgggca gttgaatttg agaaggagtt gaccattctt tg                                   42

SEQ ID NO: 24              moltype = DNA   length = 48
FEATURE                    Location/Qualifiers
misc_feature               1..48
                           note = Synthetic oligonucleotide
source                     1..48
                           mol_type = other DNA
                           organism = synthetic construct
SEQUENCE: 24
gaagctggtt ggagtaatta cggaggtggt aaccaaatcg gtttgatc                             48

SEQ ID NO: 25              moltype = DNA   length = 48
FEATURE                    Location/Qualifiers
misc_feature               1..48
                           note = Synthetic oligonucleotide
source                     1..48
                           mol_type = other DNA
                           organism = synthetic construct
SEQUENCE: 25
gatcaaaccg atttggttac cacctccgta attactccaa ccagcttc                             48

SEQ ID NO: 26              moltype = DNA   length = 48
FEATURE                    Location/Qualifiers
misc_feature               1..48
                           note = Synthetic oligonucleotide
source                     1..48
                           mol_type = other DNA
                           organism = synthetic construct
SEQUENCE: 26
gaggctggtt ggtccaacta cggtggaggt aatcaaatag gtcttatt                             48

SEQ ID NO: 27              moltype = DNA   length = 48
FEATURE                    Location/Qualifiers
misc_feature               1..48
                           note = Synthetic oligonucleotide
source                     1..48
                           mol_type = other DNA
                           organism = synthetic construct
```

```
SEQUENCE: 27
aataagacct atttgattac ctccaccgta gttggaccaa ccagcctc                48

SEQ ID NO: 28          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 28
aaatataatg ttaaagtagg agattacgtc aaggctggtc aaatcatc                48

SEQ ID NO: 29          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 29
gatgatttga ccagccttga cgtaatctcc tactttaaca ttatattt                48

SEQ ID NO: 30          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 30
aagtacaacg tcaaggtcgg tgactatgtc aaagctggtc aaataatc                48

SEQ ID NO: 31          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 31
gattatttga ccagctttga catagtcacc gaccttgacg ttgtactt                48

SEQ ID NO: 32          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 32
ggtcttattg aaaatgatgg agtgcacaga caatggtaca tgcacttg                48

SEQ ID NO: 33          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 33
caagtgcatg taccattgtc tgtgcactcc atcattttca ataagacc                48

SEQ ID NO: 34          moltype = DNA   length = 48
FEATURE                Location/Qualifiers
misc_feature           1..48
                       note = Synthetic oligonucleotide
source                 1..48
                       mol_type = other DNA
                       organism = synthetic construct
SEQUENCE: 34
ggtttgatcg agaacgacgg tgtccataga caatggtata tgcatcta                48

SEQ ID NO: 35          moltype = DNA   length = 48
FEATURE                Location/Qualifiers
misc_feature           1..48
                       note = Synthetic oligonucleotide
source                 1..48
                       mol_type = other DNA
```

-continued

```
                          organism = synthetic construct
SEQUENCE: 35
tagatgcata taccattgtc tatggacacc gtcgttctcg atcaaacc                      48

SEQ ID NO: 36             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 36
aactccttct cccaatccac cgctcaa                                            27

SEQ ID NO: 37             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 37
ttgagcggtg gattgggaga aggagtt                                            27

SEQ ID NO: 38             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 38
aactccttct ccgactccac cgctcaa                                            27

SEQ ID NO: 39             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 39
ttgagcggtg gagtcggaga aggagtt                                            27

SEQ ID NO: 40             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 40
aactccttct cctcctccac cgctcaa                                            27

SEQ ID NO: 41             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 41
ttgagcggtg gaggaggaga aggagtt                                            27

SEQ ID NO: 42             moltype = DNA   length = 27
FEATURE                   Location/Qualifiers
misc_feature              1..27
                          note = Synthetic oligonucleotide
source                    1..27
                          mol_type = other DNA
                          organism = synthetic construct
SEQUENCE: 42
aactccttct ccaacccaac cgctcaa                                            27

SEQ ID NO: 43             moltype = DNA   length = 27
FEATURE                   Location/Qualifiers
misc_feature              1..27
                          note = Synthetic oligonucleotide
source                    1..27
```

-continued

```
                          mol_type = other DNA
                          organism = synthetic construct
SEQUENCE: 43
ttgagcggtt gggttggaga aggagtt                                               27

SEQ ID NO: 44            moltype = DNA   length = 27
FEATURE                  Location/Qualifiers
misc_feature             1..27
                          note = Synthetic oligonucleotide
source                   1..27
                          mol_type = other DNA
                          organism = synthetic construct
SEQUENCE: 44
ttctccaact ccgctgctca agaccca                                               27

SEQ ID NO: 45            moltype = DNA   length = 27
FEATURE                  Location/Qualifiers
misc_feature             1..27
                          note = Synthetic oligonucleotide
source                   1..27
                          mol_type = other DNA
                          organism = synthetic construct
SEQUENCE: 45
tgggtcttga gcagcggagt tggagaa                                               27

SEQ ID NO: 46            moltype = DNA   length = 25
FEATURE                  Location/Qualifiers
misc_feature             1..25
                          note = Synthetic oligonucleotide
source                   1..25
                          mol_type = other DNA
                          organism = synthetic construct
SEQUENCE: 46
atgagatttc cttcaatttt tactg                                                 25

SEQ ID NO: 47            moltype = DNA   length = 24
FEATURE                  Location/Qualifiers
misc_feature             1..24
                          note = Synthetic oligonucleotide
source                   1..24
                          mol_type = other DNA
                          organism = synthetic construct
SEQUENCE: 47
caccgtcgtt ctcgatcaaa ccga                                                  24

SEQ ID NO: 48            moltype = DNA   length = 24
FEATURE                  Location/Qualifiers
misc_feature             1..24
                          note = Synthetic oligonucleotide
source                   1..24
                          mol_type = other DNA
                          organism = synthetic construct
SEQUENCE: 48
cttgatggta ccccacaaga cacc                                                  24

SEQ ID NO: 49            moltype = DNA   length = 24
FEATURE                  Location/Qualifiers
misc_feature             1..24
                          note = Synthetic oligonucleotide
source                   1..24
                          mol_type = other DNA
                          organism = synthetic construct
SEQUENCE: 49
ctccatcatt ttcaataaga ccta                                                  24

SEQ ID NO: 50            moltype = DNA   length = 24
FEATURE                  Location/Qualifiers
misc_feature             1..24
                          note = Synthetic oligonucleotide
source                   1..24
                          mol_type = other DNA
                          organism = synthetic construct
SEQUENCE: 50
ctttatagtt ccccaaagaa cacc                                                  24

SEQ ID NO: 51            moltype = DNA   length = 24
FEATURE                  Location/Qualifiers
misc_feature             1..24
                          note = Synthetic oligonucleotide
```

-continued

```
source                  1..24
                        mol_type = other DNA
                        organism = synthetic construct
SEQUENCE: 51
attgccggaa gattggcaaa cttg                                      24

SEQ ID NO: 52           moltype = DNA   length = 24
FEATURE                 Location/Qualifiers
misc_feature            1..24
                        note = Synthetic oligonucleotide
source                  1..24
                        mol_type = other DNA
                        organism = synthetic construct
SEQUENCE: 52
aaaacgattt gctttctagc acgg                                      24
```

UNGLYCOSYLATED LYSOSTAPHIN VARIANT PROTEIN

INTRODUCTION

This application claims priority from U.S. Provisional Patent Application Ser. No. 61/862, 599, filed Aug. 6, 2013, the content of which is incorporated herein by reference in its entirety.

SEQUENCE LISTING

The instant application contains a Sequence Listing which has been submitted electronically in XML format and is hereby incorporated by reference in its entirety. Said XML file, created on Nov. 7, 2024, is named 755528_SBT-002USCONDV_ST26.xml and is 69,149 bytes in size.

This invention was made with government support under Grant Number 1R21 AI098122 awarded by the National Institutes of Health. The government has certain rights in the invention.

BACKGROUND

*Staphylococcus aureus* is an important bacterial pathogen that causes a range of potentially life-threatening infections including skin lesions (Pantosti, A. and M. Venditti. 2009. *Eur. Respir. J.* 34:1190-1196), lung infections (Defres et al. 2009. *Eur. Respir. J.* 34:1470-1476), bacteremia (Wisplinghoff et al. 2004. *Clin. Infect. Dis.* 39:309-317), and endocarditis (Fowler et al. 2005. *JAMA* 293:3012-3021). Despite the medical community's efforts to more effectively combat this pathogen, cases of hospital and community acquired *S. aureus* infections have been rising in recent decades (Hospital Infections Program. 1999. *Am. J. Infect. Control* 27:520-532), and the incidence of antibiotic resistance in clinical isolates has also been growing steadily (Taubes, G. 2008 *Science* 321:356-361). Public health officials and healthcare providers have been deeply troubled by the emergence and rapid spread of Methicillin-resistant *Staphylococcus aureus* (MRSA), which now represents more than 50% of *S. aureus* isolates in hospital and some community settings (Grundmann et al. 2006. *Lancet* 368:874-885). Moreover, MRSA has been known to acquire additional resistance elements, thereby generating dangerous multi-drug resistant strains. Of particular concern are MRSA isolates exhibiting reduced susceptibility to vancomycin, widely considered the "drug of last resort" for MRSA infections (Taubes, G. 2008 *Science* 321:356-361). In aggregate, these data underscore an urgent need for development of novel anti-staphylococcal agents that act via mechanisms orthogonal to those of conventional antibacterial chemotherapies (Lowy, F. D. 2007. *Nat. Med.* 13:1418-1420).

Lysostaphin (LST) is a glycyl-glycine zinc-dependent endopeptidase natively encoded on the pACK1 plasmid of *Staphylococcus simulans* (Gargis et al. 2010. *Plasmid* 64:104-109), an environmental competitor of *S. aureus*. The LST enzyme selectively and efficiently degrades pentaglycine crosslinks in the peptidoglycan component of *S. aureus* cell walls, ultimately resulting in bacterial lysis and death. LST was discovered in the 1960's (Schindler, C. A. and V. T. Schuhardt. 1964. *Proc. Natl. Acad. Sci. USA* 51:104-109), and has since undergone varying degrees of preclinical development and even small scale clinical testing by different groups and organizations (Harrison et al. 1975. *Infect. Immun.* 11:309-312; Zygmunt, W. A. and P. A. Tavormina. 1972. *Prog. Drug Res.* 16:309-333; Walsh et al. 2003.

*Antimicrob. Agents Chemother.* 47:554-558; Stark et al. 1974. *New Engl. J. Med.* 291:239-240; Martin, R. R. and A. White. 1968. *J. Lab. Clin. Med.* 71:791-797). Early interest in LST as a therapeutic agent waned as a result of ready access to conventional drugs such as methicillin, but enthusiasm for LST biomedical applications has been revived due to wide spread antibiotic resistance and shallow antimicrobial development pipelines (Szweda et al. 2012. *Appl. Microbiol. Biotechnol.* 96:1157-1174).

One barrier to LST clinical applications are the high doses required to eradicate some infections. LST appeared to show good efficacy in an unresponsive leukemia patient suffering from multi-drug resistant staphylococcal pneumonia, multiple abscesses, and cellulitis (Walsh et al. 2003. *Antimicrob. Agents Chemother.* 47:554-558), but this effect required a 500 mg systemic bolus of enzyme. In another study, nasal carriers of coagulase-positive *S. aureus* were shown to be effectively cleared of the pathogen following intranasal LST treatment, but this effect again required large quantities of enzyme (one week of three times per day nasal flushing with 5 mg/ml LST solution) (Martin, R. R. and A. White. 1968. *J. Lab. Clin. Med.* 71:791-797). Similar results, at similar high dose levels, were obtained in other human studies of nasal carriage clearance (Quickel et al. 1971. *Appl. Microbiol.* 22:446-450; Harris et al. 1967. *Antimicrob. Agents Chemother.* 7:110-112). In a murine model of catheter-associated *S. aureus* biofilms, systemic LST administration to clear established biofilms during a 4-day treatment regimen, and a single prophylactic dose prevented subsequent biofilm formation on indwelling catheters (Kokai-Kun et al. 2009. *J. Antimicrob. Chemother.* 64:94-100). Extrapolating the effective doses to a human patient, however, would require more than 16 grams of enzyme to be administered over four days. Thus, while LST has demonstrated consistent efficacy in animal models and even human studies, translating the effective dosages to wide spread clinical use will require a particularly efficient production platform.

Towards this end, LST has been produced in a wide range of microbial expression hosts. For example, lysostaphin genes have been expressed in *B. subtilis* cells (Zhdaova et al. 2001. *Zh. Mikrobiol. Epidemiol. Immunobiol.* 4:3-6). One source of commercial LST is high cell density cultures of the native organism *Staphylococcus simulans*, but industrial scale production yields from this system are withheld as proprietary information. Alternatively, expression yields from the bacterial host *Escherichia coli* are known to range from 10 to 20 mg/L (Sweda et al. 2001. *Protein Expr. Purif.* 22:467-471; Szweda et al. 2005. *J. Biotechnol.* 117:203-213; Sharma et al. 2006. *Protein Expr. Purif.* 45:206-215), and this recombinant platform is also a significant contributor to commercially sourced material. Large scale LST production for clinical trials has been pursued with the *Lactococcus lactis* NICE system (Mierau et al. 2005. *Microb. Cell Fact.* 4:15; Mierau et al. 2005. *Microb. Cell Fact.* 4:16). Expression levels of 100 mg/L were achieved in large volume high cell density fermentations, but the final purified yields were only 40 mg/L (Mierau et al. 2005. *Microb. Cell Fact.* 4:15). Subsequent process optimization of this system increased bioreactor expression levels to 300 mg/L (Mierau et al. 2005. *Microb. Cell Fact.* 4:16), but there remains considerable room for further improvement. Finally, it bears noting that LST has also been expressed in mammalian cells (Williamson et al. 1994. *Appl. Environ. Microbiol.* 60:771-776), but no effort was made toward maximizing or even quantifying yields.

Several patents and patent applications have described the production of LST in a variety of microbial expression systems. For example, U.S. Patent No. 4,931,390 and EP0299978 disclose expression of a cloned LST gene in *E. coli*, *B. subtilis* and *B. sphaericus*. U.S. Patent Application No. 2002/040924 and WO 2003/082184 disclose the production of a recombinant LST protein in homogeneous form in *E. coli*, *L. lactis* and *B. sphaericus* cells. U.S. Pat. No. 6,897,041, WO 2001/029201, EP1224271, and KR1020020064886 all disclose a method of expressing recombinant LST in *E. coli*. U.S. Patent Application No. 2002/0006406 discloses analogs and variants of LST that can carry a single mutation and can be recombinantly expressed. The production of the variant is in *B. sphaericus* and the variant has a single mutation at position 218 of wild-type LST. U.S. Patent Application No. 2005/0118159 discloses truncated LST molecules with enhanced staphylytic activity. The production is in *E. coli*, *L. lactis* or *B. sphaericus*. U.S. Patent Application No. 2008/0095756 discloses LST variants and methods of use. The variants are described as being "deimmunized" molecules, meaning T-cell epitopes and domains have been removed from the LST sequence. U.S. Patent Application No. 2009/0186380 discloses methods of expressing LST in *E. coli* as well as a series of mutant LST molecules. Finally, U.S. Pat. No. 8,241,901, U.S. Application No. 2007/009351 and KR102008018960 disclose methods of expressing LST at high levels in *E. coli*. None of the methods disclosed in these patents and patent applications involve LST expression in yeast.

LST represents a promising therapeutic agent for the treatment of staphylococcal infections, in particular those of MRSA strains. However, as discussed above, conventional expression systems for the enzyme suffer from various limitations, and there remains a need for an efficient and cost-effective production process to facilitate clinical translation and development of non-medical applications.

*Pichia pastoris* is a yeast organism that has proven to be a highly successful heterologous expression host in recent years (Cregg et al. 2009. *Methods Enzymol.* 463:169-189). Unlike the prokaryotic systems that have been routinely used, *P. pastoris* has dedicated, high-capacity protein secretion pathways, which greatly simplify both upstream and downstream protein purification (Gasser et al. 2013. *Future Microbiol.* 8:191-208). Moreover, as a yeast organism, *P. pastoris* produces no endotoxins, obviating the need for arduous and inefficient endotoxin removal steps prior to biomedical applications (Vogl et al. 2013. *Curr. Opin. Biotechnol.* Doi:pii:S0958-1669(13)00038-4.10.1016/j.copbio.2013.02.024). While *Pichia pastoris* is widely used for high level production of recombinant proteins, there are two major barriers to production of LST in this industrially relevant host: lack of expression from the wild type lysostaphin gene, and aberrant glycosylation of the wild type protein sequence.

BRIEF DESCRIPTION OF THE DRAWINGS

FIG. 1A is a schematic representation of the chimeric WT-SYN genes examined. In FIG. 1B, LST expression levels from the panel of chimeric genes are presented, as measured by quantitative densitometry of SDS-PAGE protein bands.

SUMMARY OF THE INVENTION

Figure 1A:
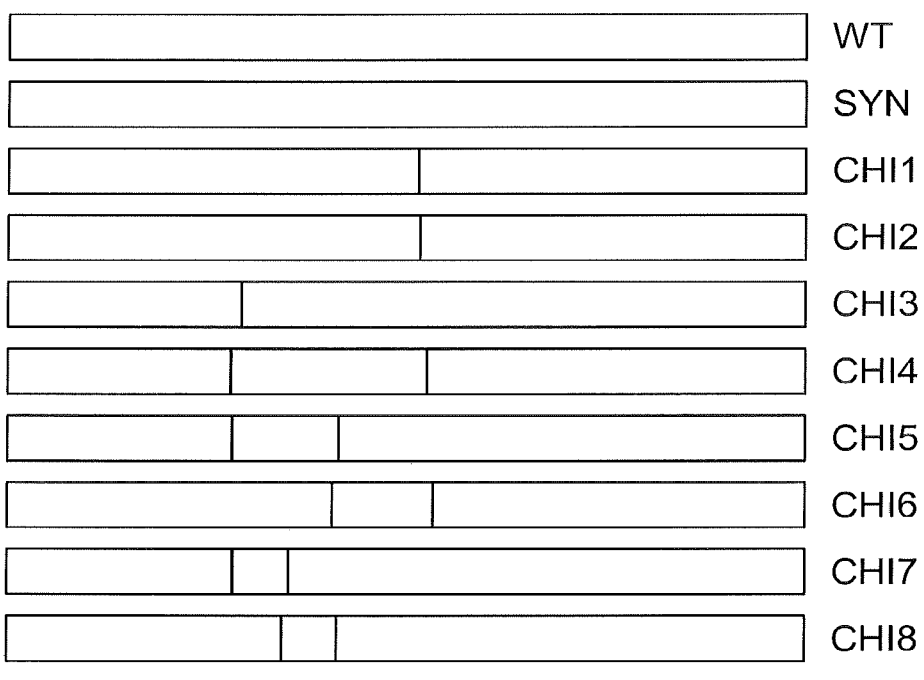
FIGS. 1A-1B depict the mapping of dominant detrimental sequences in the wild-type LST gene.

The present invention is a method for production of unglycosylated lysostaphin (LST) variant protein in a yeast expression system. The method of production involves introducing a LST variant nucleic acid molecule into *Pichia pastoris* to produce a LST-expressing *P. pastoris* organism, culturing the *P. pastoris* organism in a bioreactor culture system, and isolating the non-glycosylated LST protein or protein variant from the bioreactor culture system. In preferred embodiments, the LST nucleic acid molecule comprises the synthetic wild-type LST nucleic acid molecule of SEQ ID NO:3; the synthetic LST variant nucleic acid molecule of SEQ ID NO: 5, also referred to as LST (S126P); or the synthetic LST variant nucleic acid molecule of SEQ ID NO:7, also known as LST(T127A). Also preferred are methods of production wherein the bioreactor includes a low salt Bifidius selective media (BSM) and is maintained at 20° C. throughout the culture period. Based on the production using the method of the present invention, the present invention also includes an unglycosylated LST variant protein of SEQ ID NO:8; SEQ ID NO:4, also known as LST (S126P) protein; and a LST variant protein of SEQ ID NO: 6, also known as LST (T127A) protein. In addition, this invention provides recombinant nucleic acid molecules encoding the LST variant proteins, as well as vectors, e.g., expression vectors, and recombinant host cells harboring such vectors.

The unglycosylated LST variant proteins of this invention have been shown to have activity to prevent bacterial growth at levels similar to wild-type LST protein and can therefore be provided in a pharmaceutical composition for use in a method of inhibiting the growth of bacteria. The method of the present invention, which produces variant LST proteins, provides a cost-effective, efficient method that avoids the production of endotoxins. As a result, the present invention also includes therapeutic proteins and use of those proteins to prevent or treat bacterial infections.

DETAILED DESCRIPTION OF THE INVENTION

The present invention is directed to efficient, high level production methods of LST from the yeast expression system *Pichia pastoris*. It has now been found that low level expression of LST in yeast systems can be ascribed to premature transcription termination, which has been overcome by removing these A/T-rich gene segments, yielding a more balanced nucleotide distribution. With respect to the issue of aberrant glycosylation of wild-type LST, aberrant N-linked glycosylation at one of two consensus sequins, Asn-Xaa-Ser or Asn-Xaa-Thr, was shown to severely compromise the activity of wild-type LST (SEQ ID NO:1). While mutation of the N-linked asparagine (N125) in the centrally located Asn-Ser-Thr (NST) sequon eliminated glycosylation, it also caused a 90% decrease in catalytic performance. In contrast, substitutions at the second and third amino acids of the sequon allowed secretion of homogeneously non-glycosylated LST variants (SEQ ID NO:4 and SEQ ID NO:6) possessing full wild-type LST activity. Using methods of the present invention, the LST variants can be produced at approximately 500 mg/L in a small scale bioreactor, and 50% of that material can be recovered at high purity with a simple two step purification process. The expression system of the present invention yields large quantities of LST enzyme exhibiting wild-type catalytic activity and no contaminating endotoxin.

Experiments were performed to express the LST gene in a yeast. The first yeast system explored was *Saccharomyces cerevisiae*, where the wild-type LST gene (SEQ ID NO:2) was cloned and expressed. However, expression yields were poor despite the fact that lytic activity could be detected in culture supernatants. The next system used for experimentation was *P. pastoris*. Because of the lack of endotoxin and high inherent capacity for recombinant protein expression and secretion, *P. pastoris* has gained popularity as a cost-effective production platform for therapeutic proteins. Thus, in an effort to obtain higher expression yields from a yeast organism, the wild-type LST gene (SEQ ID NO:2) was cloned into a *P. pastoris* expression vector, pPIC9, and transformed into *P. pastoris* strain GS115. This construct deleted the native pre-pro sequence of wild-type LST and fused the enzyme to the alpha mating factor secretion signal from *P. pastoris*. Following induction of the GS115 host, however, no LST enzyme (SEQ ID NO:1) could be detected by SDS-PAGE analysis of shake flask culture supernatants. Similar results have been reported for other genes where expression levels have been found to be low to undetectable (Sinclair, G. and F. Y. Choi. 2002. *Protein Expr. Purif.* 26:96-105). It is known that protein secretion from *P. pastoris* is a multiple step process involving transcription, translation, protein folding, and translocation through the secretory pathway to the culture media. Any one of these steps may be rate-limiting for a given protein target (Delic et al. 2013. *FEMS Microbiol. Rev.* doi:10.1111/1574-6976.12020; Love et al. 2012. *PLoS One* 7:e37915). Thus, while *P. pastoris* has advantages for biotherapeutic production, obtaining high level expression has been problematic.

It was initially believed that the lack of any detectable expression of LST in *P. pastoris* was a result of differential codon bias in the bacterial gene verses the yeast host (Table 1), but a closer inspection of the wild-type LST gene also revealed three stretches of DNA exhibiting strikingly high A+T content ([34]AATAATTACAAAAAA[48] (SEQ ID NO:9), [107]ATTTTTTTATGAATATT[123] (SEQ ID NO:10) and [252]TAAATATAATGTTAAA[267] (SEQ ID NO:11) of the wild-type LST gene (SEQ ID NO:2)). Thus, it was also possible that one or more internal segments of the wild-type gene were serving as premature transcription termination signals (Scorer et al. 1993. *Gene* 136:111-119; Schuren, F. H. and J. G. Wessels. 1998. *Curr. Genet.* 33:151-156).

TABLE 1

| Gene | Identity to Wild-Type (%) | G + C (%) | CAI | CBI | Fop |
|---|---|---|---|---|---|
| Wild-Type | 100 | 37.4 | 0.113 | −0.035 | 0.388 |
| SYN | 75 | 52.7 | 0.877 | 0.963 | 0.978 |

CAI, Codon Adaptation Index;
CBI, Codon Bias Index;
Fop, Frequency of optimal codons.

To address these potential issues simultaneously, an the artificial gene encoding wild-type LST enzyme, synthetic LST or SYN LST (SEQ ID NO:3), was synthesized to satisfy two general objectives: (1) substituting the preferred codon usage of *P. pastoris*, and (2) balancing the A+T/C+G distribution of segments with disproportionate A+T content. In the SYN gene, most codons were replaced by the most preferred codons of *P. pastoris*. However, to disrupt long stretches of A/T bases, the second most frequent *P. pastoris* Thr and Val codons were inserted as needed. Specifically, ACC (14.5% usage) instead of ACT (22.4% usage) was occasionally used for Thr, and GTC (14.9%) instead of GTT (26.9%) was used for Val. Differences in the characteristics of the wild-type and SYN gene are listed in Table 1. In contrast to the wild-type gene, expression of the SYN gene from *P. pastoris* yielded substantial quantities of enzyme in the culture supernatant (~80 mg/L in shake flask culture).

Figure 1B:
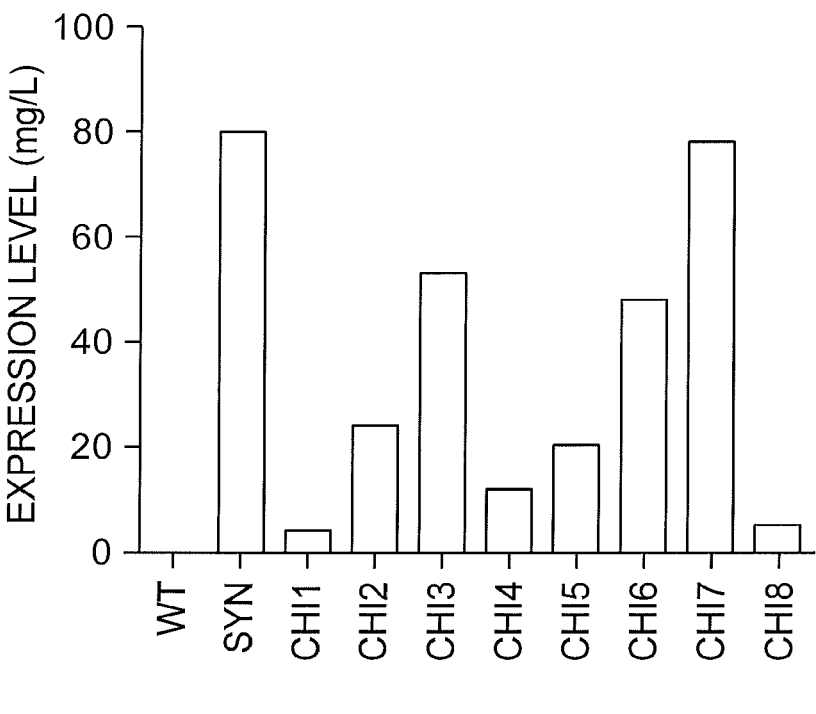

To identify specific regions of the wild-type LST gene that were responsible for poor expression, a panel of chimeric WT-SYN genes was constructed. Sequences that contributed most to compromised expression were traced through a series of studies in which constituent wild-type gene sequence was systematically split in two, and each half was replaced by the corresponding SYN sequence. Expression from the two resulting constructs was compared head-to-head, and the lower yielding chimera was fed into the next round of wild-type sequence splitting and replacement. FIG. 1A depicts the chimeric constructs and a map of the dominant detrimental sequences in the wild-type LST gene. While the complete failure of wild-type LST expression could not be traced to any single region of the gene, it was found that detrimental sequences were not evenly distributed (FIG. 1B). Importantly, the most critical determinant of poor expression yields was confined to a 49 base pair segment (Chi8) from nucleotides 228 to 276 located in the wild-type gene (SEQ ID NO:2).

Experiments were subsequently performed to examine the mechanism of the compromised expression in LST. A detailed sequence comparison of base pairs 228 to 276 of wild-type and SYN genes revealed that the key differences were located within an A+T-rich region (from nucleotides 252 to 267), as opposed to being associated with any highly under-represented codon bias (Table 2).

TABLE 2

| LST Gene | Nucleotides 228 to 276 | SEQ ID NO: |
|---|---|---|
| Wild-Type | TAGACAATGGTATATGCATCTAAG TAAATATAATGTTAAAGTAGGAGA T | 12 |
| SYN | CAGACAATGGTACATGCACTTGTC CAAGTACAACGTCAAGGTCGGTGA C | 13 |
| SYN+AT | CAGACAATGGTACATGCACTTGTC TAAATATAATGTTAAAGTCGGTGA C | 14 |
| WT-ΔAT | *TAGACAATGGTATATGCATCTAAG CAAGTACAACGTCAAGGTAGGAGA T* | 15 |

Nucleotides 252 to 267 are underlined.

To confirm the regulatory role of this A+T rich region, the wild-type A+T rich segment (nucleotides 252 to 267) was spliced into the SYN LST gene yielding construct SYN+AT.

This gene was essentially a more narrowly focused daughter of chimeric gene Chi8. Additionally, the same A+T rich segment was deleted from the wild-type LST gene by substitution of the corresponding SYN sequence, thereby yielding gene WT-ΔAT, the inverse of gene SYN+AT. See Table 2. Analysis of culture supernatants by SDS-PAGE revealed that deletion of the A+T rich region in WT-ΔAT resulted in enhanced LST expression, although at lower levels than observed with SYN LST. In contrast, introduction of the A+T rich region in the SYN+AT gene did not reduce expression compared to SYN LST.

In order to determine if the A+T rich region was influencing as expression by acting a premature transcription terminator, experiments performed with RT-PCR to detect mRNAs corresponding to the full-length wild-type and SYN LST genes, or shorter 5'-fragments thereof. This analysis indicated that expression levels were found to correlate well with the relative abundance of mRNA. In particular, no LST-specific mRNA was detected for the WT LST gene, high level mRNA was detected for the SYN LST gene, and low level mRNA was detected for the WT-□AT gene.

To evaluate the potential of *P. pastoris* for pilot scale production of LST, SYN LST expressing *P. pastoris* was cultured in a 2 liter (L) bioreactor. Induction at low temperature (20° C.) prevented the degradation of LST, and using low salt Bifidius selective media (BSM) increased the polyethylene glycol (PEG) precipitation efficiency. Expression levels from bioreactor cultivations were ~500 mg/L, and approximately 50% of this material could be recovered in high purity by PEG precipitation and cation exchange chromatography. However, LST from both shake flask and bioreactor cultures migrated as doublets in SDS-PAGE. The two species co-eluted from cation exchange chromatography as a single peak, and reducing the mass of enzyme loaded on the FPLC column did not increase chromatographic resolution. The higher molecular weight material was thought to result from aberrant glycosylation, and indeed the upper band disappeared from SDS-PAGE after PNGase F treatment. Consistent with prior observations that glycosylated LST from mammalian cells is inactive (Kerr et al. 2001. *Nat. Biotechnol.* 19:66-70), FPLC fractions containing a higher proportion of glycosylated were less active in turbidometric assays. Thus, there was a need to generate non-glycosylated variants to take full advantage of the *P. pastoris* expression host.

Experiments were performed, therefore, to construct non-glycosylated LST variants and then analyze their activity. LST contains two consensus N-linked glycosylation sequons, one at position 125 ($^{125}$Asn-Ser-Thr$^{127}$) and the other at position 232 ($^{232}$Asn-Lys-Thr$^{234}$). When the latter, position 232, was disrupted with an N232Q point mutation, the variant protein continued to migrate as a doublet in SDS-PAGE. This result indicated that N125 was the site of aberrant glycosylation in *P. pastoris*. Additional evidence for this conclusion was provided by the recent demonstration that position N125 is the site of glycosylation in mammalian cells (Huang et al. 2013. *Anim. Biotechnol.* 24:129-147).

Figure 2:
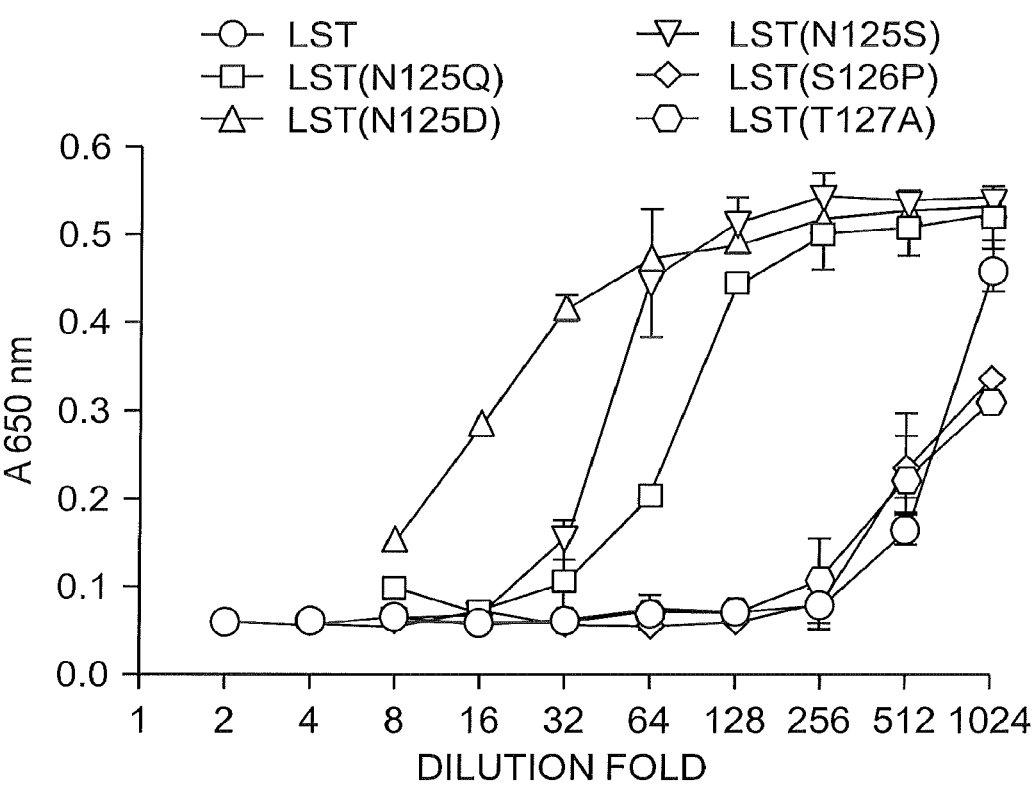
FIG. 2 depicts results of experiments to examine the effect of aglycosylation on LST activity. It was found that unconventional sequon mutations enhanced the performance of non-glycosylated LST. MIC assays with *S. aureus* SA113 were performed on 2-fold serial dilutions of culture supernatants. The OD650 readings for each dilution of each enzyme are shown. Note that the three most active enzymes attained the MIC-50 between 512- and 1024-fold dilution levels. Error bars represent the standard deviation.

The N125 glycosylation sequon was initially disrupted via a strategy wherein a conservative N->Q point mutation was introduced at position 125. The mutation successfully abolished *P. pastoris* glycosylation of LST, and yielded expression levels that were comparable to that of the wild-type protein. Surprisingly, however, MIC-50 analysis of culture supernatants showed the aglycoslyated N125Q variant to exhibit 10-fold lower activity than *P. pastoris* produced native enzyme (FIG. 2).

Given the unexpected out come with the N125Q mutation, four additional non-glycosylated mutants were constructed, expressed, and analyzed (Table 3). Two of the mutants included alternative substitutions at position 125 (N125D and N125S), one at position 126 (S126P), and one at position 127 (T127A). Similar to the original results with N125Q, the four newly mutated enzymes were uniformly non-glycosylated and expressed at levels comparable with the wild-type protein. Interestingly, the alternative N125D and N125S mutations caused even greater reductions in antibacterial activity (17-fold and 42-fold, respectively) (FIG. 2). In contrast, the LST(S126P) variant of SEQ ID NO:4, and LST(T127A) variant of SEQ ID NO:6, possessed bactericidal activity equivalent to that of the wild-type protein (FIG. 2).

TABLE 3

| LST | Sequon 125-127 | Sequon 232-234 |
| --- | --- | --- |
| Wild-Type | NST | NKS |
| LST(N125Q) | QST | NKS |
| LST(N125D) | DST | NKS |
| LST(N125S) | SST | NKS |
| LST(N126P) | NPT | NKS |
| LST(T127A) | NSA | NKS |

Figure 3:
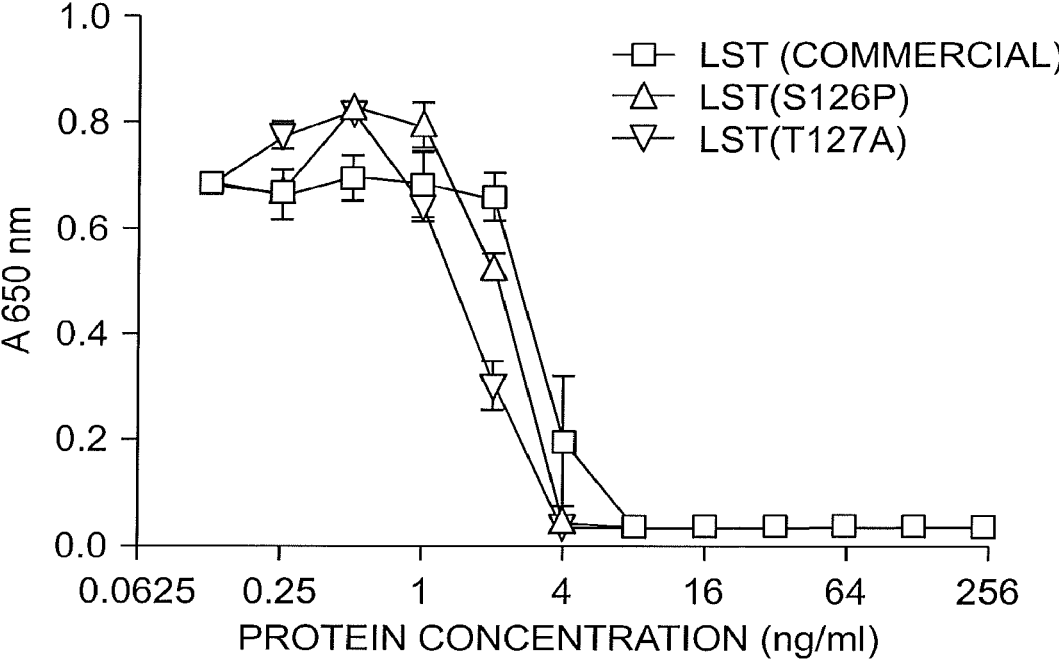
FIG. 3 depicts results of experiments analyzing the activity of non-glycosylated LST variants. The results shown are from experiments to examine the antibacterial efficacy of the LST variants as measured by a Minimum Inhibitory Concentration (MIC) assay. Serial dilutions of purified enzymes were evaluated for growth inhibition of *S. aureus* strain SA113. Results shown are OD650 readings after 24 hours of growth.

These two variants were therefore selected for further study. LST(S126P) and LST(T127A) variants were expressed in a 2 L bioreactor and purified to homogeneity following the same production process as for wild-type LST. The expression levels and final purified yields were very similar for both of the non-glycosylated variants (SEQ ID NO:4 and SEQ ID NO:6) and wild-type LST (SEQ ID NO:1). The activity and thermostability of non-glycosylated LST variant proteins were compared with commercially sourced LST as a reference. In turbidometric assays of lysis kinetics, the TOD$_{50}$ (the time to achieve a 50% reduction in turbidity of *S. aureus* cell suspensions) of LST(S126P), LST(T127A) and commercial LST were 5, 7 and 17 minutes, respectively. Similarly, in antibacterial minimum inhibitory concentration (MIC) assays, LST(S126P) and LST(T127A) exhibited 2-fold improved efficacy compared to that of the commercial enzyme (MIC-0 of 4 ng/ml for LST(S126P) and LST(T127A) verses 8 ng/ml for commercial enzyme) (FIG. 3). With respect to structural stability, LST(S126P) showed a single apparent Tm of 57° C. and LST(T127A) a single Tm of 59° C. This is in contrast to commercially sourced wild-type LST, which exhibited two distinct transitions, one at 47° C. and another at 60° C. These differences in activity and stability between LST variant proteins and wild-type LST protein may be attributed to the engineered point mutations, the yeast verses bacterial expression platforms, differences in the respective purification processes, or some combination of these elements. Regardless, when considered together, these results clearly demonstrated that non-glycosylated LST protein variants of SEQ ID NO:4 and SEQ ID NO:6, produced from *P. pastoris*, outperformed commercially sourced LST of bacterial origin.

Results of the experiments described herein demonstrate that the initial lack of detected LST in *P. pastoris* culture supernatants was traced to a transcriptional bottleneck, which was alleviated by use of a codon-manipulated synthetic gene that coded for the native LST protein sequence. Implementing a systematic "divide and conquer" approach, the wild-type and synthetic genes were recombined, and a dominant premature transcription termination signal was confined to nucleotides 228-276 of the wild-type LST gene. Significantly, substitution of an even smaller 16 base pair A+T-rich tract of the wild-type sequence (construct WT+AT) with the corresponding synthetic sequence yielded moderate expression levels corresponding to 25% that of the synthetic gene. Thus, this short A+T-rich segment is a key element of the dominant internal LST transcription terminator. It bears noting, however, that swapping this short A+T-rich tract between the two genes neither recovered the full expression level of the complete synthetic gene (in the case of WT-ΔAT) nor reduced expression levels of the synthetic gene by any discernible degree (in the case of SYN+AT). Therefore, it seems that the broader context of the 16 base pair A+T-rich sequence is important, and likewise there appears to be other minor premature transcription termination signals embedded within wild-type LST gene. In aggregate, the results presented herein support a relatively refined mechanism for the lack of *P. pastoris* expression from the wild-type LST gene.

Gene sequence mutation has been a widely effective measure to increase heterologous protein expression levels in *P. pastoris* (Nakamura et al. 2013. *Biotechnol. Appl. Biochem*:doi:10.1002/bab.1079; Hu et al. 2013. *PLoS One* 8:e58393; Yang et al. 2013. *PLoS One* 8:e53939; Tu et al. 2013. *Appl. Microbiol. Biotechnol*. 97:2867-2875; Chung et al. 2012. *BMC Syst. Biol.* 6:134), but the mechanism behind this strategy has been seldom studied. The model presented herein has important implications with respect to codon usage for high level gene expression in *P. pastoris*. According to the model, premature transcription termination may result from short segments of severe nucleotide bias within some native genes, and targeted disruption of these regions may represent an efficient and cost-effective strategy for gene mutation. As shown here, substitution of only six nucleotides was sufficient to activate reasonable expression from the otherwise incompetent wild-type LST gene. The results herein indicate that A+T-rich regions should be considered as primary targets for mutagenesis.

Aberrant glycosylation is a frequently encountered barrier to high level production of functional protein from *P. pastoris*, and this has been shown to be the case for the antibacterial enzyme LST. In most instances, destruction of the glycosylation sequon is accomplished by substituting the N-linked asparagine residue with glutamine, aspartic acid, serine, or alanine (Zhao et al. 2009. *FEMS Yeast Res.* 9:591-599; Muller-Steffner et al. 2010. *Protein Expr. Purif.* 70:151-157; Vinzon et al. 2010. *Protein Expr. Purif.* 73:23-30; Peraino et al. 2012. *Protein Expr. Purif.* 82:270-278). In the experiments described here, all mutations at the N-linked N125 residue led to significantly (10-fold or greater) decreased enzyme activity. The severely compromised activity of the N125 mutants was surprising given the fact that residue 125 is thought to reside in a linker between the functional M23 peptidase domain and SH3-like cell wall binding domain (UniProt entry P10547). Thus, for the first time, it has been shown that the choice of mutation position in a glycosylation sequon can influence the functionality of non-glycosylated protein variants. This knowledge could greatly enhance the utility of LST in transgenic animals, and more generally, other functionally sensitive proteins may benefit from a broadened choice of mutations for N-linked sequon disruption.

Thus, the present invention is an efficient, high level production system for LST in the yeast host *P. pastoris*. By a combination of nucleic acid sequence modification, protein glycosylation modification, and bioprocess modification, high expression levels (i.e., 500 mg/L) and high final purified yields (i.e., 250 mg/L) have been obtained in laboratory scale bioreactors. These high yields and the ease of purification for the secreted, endotoxin-free enzyme are important advances in the development of LST as a therapeutic agent for treating bacterial infections in mammals, including humans.

Thus, the present invention provides recombinant nucleic acids, proteins, vectors and host cells and use of the same in a novel method to efficiently produce a LST protein that has activity equivalent to wild-type LST. The present invention, therefore is a method for production of a non-glycosylated LST variant protein in a yeast expression system, which includes the steps of: a) introducing a LST variant nucleic acid molecule into a yeast organism (e.g., by transformation or electroporation of a vector harboring the LST variant nucleic acid molecule) to produce a LST-expressing organism, wherein the LST variant is the result of mutating the wild-type LST nucleic acid to produce a nucleic acid with reduced A/T-rich segments; b) culturing the yeast organism in a bioreactor culture system; and c) isolating the non-glycosylated LST protein from the bioreactor culture system. In preferred embodiments, the yeast organism is *Pichia pastoris*. In other preferred embodiments the LST variant nucleic acid molecule comprises SEQ ID NO:5 or SEQ ID NO:7. In further preferred embodiments, the LST-expressing organism is cultured in the bioreactor in a low salt BSM media at 20° C.

Vectors of use in this invention can be used to amplify the LST variant nucleic acid molecule and/or express the LST variant protein. In this respect, a vector of the invention can include cloning vectors such as, e.g., pBLUESCRIPT, pUC19 or pBR322, which are commonly used in *E. coli* for propagation and maintenance of the LST variant nucleic acid molecule in *E. coli*, as well as expression vectors such as the pPIC vectors for expression of LST variant protein in *Pichia pastoris*; or pYES2 or pTEF1 for expression of LST variant protein *S. cerevisiae*.

Suitable recombinant hosts for propagation and maintenance of the LST variant nucleic acid molecule include any conventional strain of *E. coli* include, e.g, DH10B, HB101, JM109, DH5α or XL1-BLUE.

Suitable recombinant hosts for expressing the LST variant protein include, for example, wild-type *P. pastoris* or derivatives of *P. pastoris* strain NRRL-Y 11430 (Northern Regional Research Laboratories, Peoria, IL) such as GS115 (his4), KM71, (his4 arg4 aox1Δ::ARG4), or MC100-3 (his4 arg4 aox1Δ::SARG4 aox2Δ::Phis4), as well as *S. cerevisiae* strains DYS-5 or DYS-6, for example.

Also contemplated by the present invention are isolated LST variant proteins that can be used as therapeutics to prevent or treat diseases such as bacterial infections, wherein the bacterial infection is a *S. aureus* infection or a MRSA infection.

In the context of the present invention a "LST variant nucleic acid molecule" is a nucleic acid molecule, wherein the sequence has been mutated to produce a nucleic acid molecule with reduced A/T-rich segments compared to the wild-type nucleic acid molecule. Specifically, whereas the wild-type LST nucleic acid molecule has an A/T content of 63% and G/C content of 37%, a variant LST nucleic acid molecule encodes for LST and has an A/T content in the range of 48% to 60% and G/C content in the range of 40% to 52%. In certain embodiments, a variant LST nucleic acid molecule has an A/T content of less than 60%, 55%, 54%, 53%, 52%, 51%, 50%, 49% or 48%. Examples of LST variant nucleic acid molecules of this invention include, but are not be limited to, the sequences provided by SEQ ID NO:3, SEQ ID NO:5 and SEQ ID NO:7.

Also in the context of the present invention, a "LST variant protein" is an LST protein that is encoded by a LST nucleic acid molecule with reduced A/T-rich segments. In certain embodiments, the LST variant protein is a variant of the LST protein isolated from *Staphylococcus simulans*. Examples of LST variant proteins include, but are not limited to, proteins provided under SEQ ID NO:4, SEQ ID NO:6 and SEQ ID NO:8. In certain embodiments, the LST variant protein is not glycosylated. In accordance with this embodiment, a LST variant protein is defined as an LST protein having an amino acid substitution at one or both of position 126 ($Ser^{126}$) or 127 ($Thr^{127}$) of the wild-type LST protein (SEQ ID NO:1). Examples of suitable substitutions include, but are not limited to, e.g., substitution of $Ser^{126}$ and/or $Thr^{127}$ with a glutamine, proline, aspartic acid or alanine thereby blocking glycosylation of the LST protein. Examples of such LST variant proteins include, but are not be limited to, proteins provided under SEQ ID NO:4 and SEQ ID NO:6. In particular embodiment, the LST variant protein of the invention has a single apparent melting temperature or thermal denaturation temperature (Tm), preferably in the range of 50° C. to 59° C. In contrast, as demonstrated herein, wild-type LST has two distinct transitions, one at 47° C. and another at 60° C.

In the context of the present invention, a "nucleic acid molecule with reduced A/T-rich segments" is a nucleic acid molecule that has been mutated to replace regions having a premature transcription termination signal with alternative codons that do not include the premature transcription termination signal. Examples of such nucleic acid molecule with reduced A/T-rich segments include, but are not be limited to, SEQ ID NO:5 and SEQ ID NO:7. However, other nucleic acid molecules with reduced A/T-rich segments are envisioned. For example, expression of one of more of the following nucleic acid molecules in *P. pastoris* could be improved in accordance with the teachings of the present invention: α-galactosidase A, α-1,6 glucan-6-glucanohydrolase, penicillin G amidase, antithrombin, chicken cystatin, α-lactolbumin, cutinase, phytase, cellobiohydrolase, single-chain Fv, carcinoembryonic antigen, gelatinase B, laccase, galactose oxidase, neuroaminidase, alpha 1-antitrypsin and the like. See, e.g., Li et al. 2007. *Appl. Biochem. Biotechnol.* 142:105-124.

As also mentioned, the LST variant proteins of the present invention are of use as therapeutics for prevention or treatment of diseases that would include bacterial infections with *S. aureus* or MRSA. Therefore, the present invention also provides pharmaceutical compositions containing the LST variant protein and a method for inhibiting the growth of bacteria by contacting bacteria with an effective amount of a LST variant protein. In one embodiment, the method involves the use of an LST variant protein that has the sequence set forth in SEQ ID NO:4 or SEQ ID NO:6. In preferred embodiments, the bacteria are *S. aureus* or methicillin-resistant *S. aureus* (MRSA) bacteria. One of skill in the art would understand how to develop such protein therapeutics based on the common use of protein therapeutics in medicine today.

When used to prevent or treat a bacterial infection, the LST variant proteins would be administered to a subject in need of treatment in an amount that effectively inhibits bacterial growth or colonization. The level of inhibition of bacterial growth or colonization could range anywhere from 50% to 100%. In the context of this invention, a patient or subject can be any mammal including human, companion animals (e.g., dogs or cats), livestock (e.g., cows, sheep, pigs, or horses), laboratory animal (e.g., rabbits), or zoological animals (e.g., monkeys). In particular embodiments, the subject is a human.

For therapeutic use, the LST variant protein can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, PA, 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically, orally, intranasally, intravaginally, or rectally, according to standard medical practices.

The selected dosage level of a LST variant protein will depend upon a variety of factors including the route of administration, the time of administration, the duration of the treatment, other drugs, compounds and/or materials used in combination, the age, sex, weight, condition, general health and prior medical history of the patient being treated, and other factors well-known in the medical arts.

It is also contemplated that the LST variant protein can be used either alone or in combination with other agents commonly used to treat bacterial infections in patients. Such agents would include but not be limited to any of the known and marketed antibiotics. One of skill in the art would choose which agents to use in combination based on their clinical experience with such agents, using doses approved for use in humans per the labeling for the drug products as marketed.

A physician having ordinary skill in the art can readily determine and prescribe the effective amount of the pharmaceutical composition required based upon the administration of similar compounds or experimental determination. In the context of the present invention, an "effective amount" or an "effective dose" is defined as an amount or dose of LST variant protein that inhibits bacterial growth or colonization by at least 50%. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The efficacy of a LST variant protein that has been screened in vitro and shown to have activity to inhibit growth of bacteria, such as *S. aureus*, can be further examined using a model such as the one described by Patel et al. (2004. *Antimicrob. Agents Chemother.* 48:4754-4761). Briefly, Swiss mice (6 mice per dose group, 4 weeks of age) are inoculated intraperitoneally (i.p.) with 0.5 ml of bacterial suspension so that each mouse receives from $2 \times 10^8$ to $3 \times 10^8$ CFU of isolate. The agent to be tested, or the combination of agents to be tested, is then given at a dose shown to be effective in vitro but also known to be safe in animals. The doses to be tested are routinely chosen by those of skill in the art by using clinical judgment based on results of in vitro pharmacological assays. For example, doses can be ones that are equivalent to an ED10, an ED25, an ED50, and/or an ED75 for inhibiting bacterial growth in vitro. The agent can be administered at 1 and 4 hours after i.p. inoculation of mice with isolates. The agent to be tested can be administered subcutaneously, intravenously, or orally. A vehicle control group is also used. All mice are observed for survival up to 7 days. Efficacy of the test drug is measured as an increased survival rate as compared to control animals (untreated) and as compared to survival in a group of animals administered a positive control agent (e.g., an antibiotic known to have efficacy to treat *S. aureus*).

It is contemplated that one of skill in the art will choose the most appropriate in vivo model system depending on the type of product being developed. Some in vivo models are more amenable to oral or intravenous injection while others are more desirable for dermal application methods. The medical literature provides detailed disclosure on the advantages and uses of a wide variety of such models.

The following non-limiting examples are provided to further illustrate the present invention.

Example 1: Reagents

Primers used included those with standard desalting from IDT Technologies (Coralville, IA). Enzymes for molecular cloning and REMOVE-IT™ PNGase F were purchased from New England Biolabs (Ipswich, MA). LST produced in *Escherichia coli* was purchased from Sigma (St. Louis, MO).

Example 2: Plasmid and Strains

*P. pastoris* expression vector pPIC9 and *P. pastoris* strain GS115 were purchased from Invitrogen (Grand Island, NY). *S. aureus* strain SA113 was from the American Type Culture Collection (Manassas, VA).

Example 3: Lysostaphin Encoding Genes

The wild-type (WT) LST gene was amplified from *S. simulans* with primers WT-F and WT-R (Table 4). The synthetic (SYN) LST gene was synthesized by Shanghai Xuguan Biotechnology Development Company (Shanghai, China) and amplified with primers Syn-F and Syn-R (Table 4). The chimeric and non-glycosylated LST mutant genes were amplified by splice over-lap extension PCR with the primers listed in Table 4.

TABLE 4

| Primer | Sequence (from 5' to 3') | SEQ ID NO: |
|---|---|---|
| WT-F | ATCGCTCGAGAAAAGAGCTGCAACACAT | 16 |
| WT-R | CGATGAATTCTTACTTTATAGTTCCCCA | 17 |
| Syn-F | ATCGCTCGAGAAAAGAGCTGCTACCCAC | 18 |
| Syn -R | CGATGAATTCTTACTTGATGGTACCCCA | 19 |
| Chi1-F | CAAAGAATGGTTAATTCATTTTCCCAAT CCACCGCTCAAGAC | 20 |
| Chi1-R | GTCTTGAGCGGTGGATTGGGAAAATGAA TTAACCATTCTTTG | 21 |
| Chi2-F | CAAAGAATGGTCAACTCCTTCTCAAATT CAACTGCCCAAGAT | 22 |
| Chi2-R | ATCTTGGGCAGTTGAATTTGACAAGGAG TTGACCATTCTTTG | 23 |
| Chi3-F | GAAGCTGGTTGGAGTAATTACGGAGGTG GTAACCAAATCGGTTTGATC | 24 |
| Chi3-R | GATCAAACCGATTTGGTTACCACCTCCG TAATTACTCCAACCAGCTTC | 25 |
| Chi4-F | GAGGCTGGTTGGTCCAACTACGGTGGAG GTAATCAAATAGGTCTTATT | 26 |
| Chi4-R | AATAAGACCTATTTGATTACCTCCACCG TAGTTGGACCAACCAGCCTC | 27 |
| Chi5-F | AAATATAATGTTAAAGTAGGAGATTACG TCAAGGCTGGTCAAATCATC | 28 |
| Chi5-R | GATGATTTGACCAGCCTTGACGTAATCT CCTACTTTAACATTATATTT | 29 |
| Chi6-F | AAGTACAACGTCAAGGTCGGTGACTATG TCAAAGCTGGTCAAATAATC | 30 |
| Chi6-R | GATTATTTGACCAGCTTTGACATAGTCA CCGACCTTGACGTTGTACTT | 31 |
| Chi7-F | GGTCTTATTGAAAATGATGGAGTGCACA GACAATGGTACATGCACTTG | 32 |
| Chi7-R | CAAGTGCATGTACCATTGTCTGTGCACT CCATCATTTTCAATAAGACC | 33 |
| Chi8-F | CGTTTGATCGAGAACGACGGTGTCCATA GACAATGGTATATGCATCTA | 34 |
| Chi8-R | TAGATGCATATACCATTGTCTATGGACA CCGTCGTTCTCGATCAAACC | 35 |
| N125Q-F | AACTCCTTCTCCCAATCCACCGCTCAA | 36 |
| N125Q-R | TTGAGCGGTGGATTGGGAGAAGGAGTT | 37 |
| N125D-F | AACTCCTTCTCCGACTCCACCGCTCAA | 38 |
| N125D-R | TTGAGCGGTGGAGTCGGAGAAGGAGTT | 39 |
| N225S-F | AACTCCTTCTCCTCCTCCACCGCTCAA | 40 |
| N125S-R | TTGAGCGGTGGAGGAGGAGAAGGAGTT | 41 |
| S126P-F | AACTCCTTCTCCAACCCAACCGCTCAA | 42 |
| S126P-R | TTGAGCGGTTGGGTTGGAGAAGGAGTT | 43 |

TABLE 4-continued

| Primer | Sequence (from 5' to 3') | SEQ ID NO: |
|--------|--------------------------|------------|
| T127A-F | TTCTCCAACTCCGCTGCTCAAGACCCA | 44 |
| T127A-R | TGGGTCTTGAGCAGCGGAGTTGGAGAA | 46 |
| Alfa-F | ATGAGATTTCCTTCAATTTTTACTG | 46 |
| SSyn-R | CACCGTCGTTCTCGATCAAACCGA | 47 |
| FullSyn-R | CTTGATGGTACCCCACAAGACACC | 48 |
| 5WT-R | CTCCATCATTTTCAATAAGACCTA | 49 |
| FullWT-R | CTTTATAGTTCCCCAAAGAACACC | 50 |
| AOX1-F | ATTGCCGGAAGATTGGCAAACTTG | 51 |
| AOX1-R | AAAACGATTTGCTTTCTAGCACGG | 52 |

Example 4: *Pichia pastoris* Expression

The LST encoding genes were digested with XhoI and EcoRI, ligated into similarly digested pPIC9, and transformed by electroporation into *E. coli* DH5α [F-Φ80lacZΔM15 Δ(lacZYA-argF) U169 recA1 endA1 hsdR17 (rK–, mK+) phoA supE44 λ-thi-1 gyrA96 relA1]. This fused LST in-frame with the aplha mating factor secretion signal peptide. Clones bearing the expression vector with insert were selected by PCR and confirmed by DNA sequence analysis. The pPIC9 expression vectors harboring LST genes were digested with SacI prior to electroporation into *P. pastoris* strain GS115. *P. pastoris* transformants were screened in MD media (1.34% YNB, $4 \times 10^{-5}$% biotin, 2% dextrose, 1% agar) and cultured in BMGY/BMMY media (BMGY media: 1.0% yeast extract, 2.0% peptone, 1.34% YNB, $4 \times 10^{-5}$% biotin, 1.0% glycerol, 100 mM pH 6.0 phosphate buffer; and BMMY media: 1.0% yeast extract, 2.0% peptone, 1.34% YNB, $4 \times 10^{-5}$% biotin, 0.5% glycerol, 100 mM pH 6.0 phosphate buffer). LST expressing strains were identified by SDS-PAGE analysis of culture supernatant.

Example 5: RT-PCR

LST mRNA (5'-fragment or full length) was detected by RT-PCR using primers listed in Table 4. A fragment of alcohol oxidase 1 (AOX1) served as control.

Example 6: Bioreactor Culture

For pilot-scale production of LST, *P. pastoris* was cultured in a 2 L bioreactor as described previously (Zhao et al. 2008. *Appl. Microbiol. Biotechnol.* 81:235-241). Briefly, a 3-stage culture process was employed. First, *P. pastoris* was cultured in low salt BSM media (85% phosphoric acid 20 ml/L, calcium sulfate 0.2 g/L, potassium sulfate 5 g/L, magnesium sulfate-$7H_2O$ 4 g/L, potassium hydroxide 1 g/L, glycerol 30 g/L). After the glycerol had been exhausted, a glycerol fed-batch phase was followed to increase the cell density. Lastly, the expression of lysostaphin was induced by methanol at 20° C.

Example 7: Lysostaphin Purification

LST was precipitated from culture supernatants by 25% PEG precipitation, re-suspended in 20 mM $NaHPO_4$ PH 7.5 buffer, and bound to a HIPREP S SEPHAROSE Fast Flow column that had been equilibrated with the same buffer. LST was eluted from the column by a 0 to 250 mM NaCl gradient.

Example 8: MIC Assay

The MIC of LST was determined by the microplate method (Kusuma, C. M. and J. F. Kokai-Kun. 2005. *Antimicrob. Agents Chemother.* 49:3256-3263). Lysostaphin was serially diluted in TSB media using 96-well polystyrene plates. Each well was inoculated with ~$10^6$ CFU/ml *S. aureus* strain SA113 yielding total volumes of 100 μl per well. Microplates were then incubated at 37° C. for 24 hours. The MIC-0 and MIC-50 were defined as complete or 50% inhibition of growth, respectively, as determined by measuring light scattering at 650 nm in a microplate reader.

The bactericidal activity in the culture supernatant was determined by MIC-50, 50% inhibition of growth. The bactericidal activity of the purified LST was determined by MIC-0, complete inhibition of growth. Both MIC-0 and MIC-50 were determined by measuring light scattering at 650 nm in a microplate reader. Assays were performed in duplicate.

Example 9: Turbidity Assay

*S. aureus* strain SA113 was cultured overnight in TSB media, pelleted by centrifugation, and washed once with PBS (2.7 mM KCl, 1.5 mM $KH_2PO_4$, 8.9 mM $Na_2HPO_4$, 136.9 mM NaCl, pH 7.4). The cells were then re-suspended in a volume of PBS sufficient to yield an absorbance reading of 0.8 at 650 nm. Bacterial suspension (100 μl) was aliquoted into replicate wells of a 96-well flat bottomed polystyrene plate (NUNC 269620), and lysis reactions were initiated by adding 5 μg/ml LST to the bacterial suspension. The kinetics of bacterial lysis were followed by measuring optical density at 650 nm every minute for a total of 30 minutes, and the activity of the various LST constructs was defined as the time to reach half starting absorbance ($TOD_{50}$) of the initial bacterial suspension.

Example 10: Thermostability Assay

The thermostability of LST constructs was determined by differential scanning fluorimetry as previously described (Niesen et al. 2007. *Nat. Protoc.* 2:2212-2221) using an ABI 7500 Fast Real-Time PCR System from Applied Biosystems. Proteins and SYPRO Orange were diluted in PBS, and fluorescence was quantified from 25 to 94° C.

What is claimed is:

1. A method for inhibiting growth of bacteria, the method comprising contacting the bacteria with an effective amount of a lysostaphin (LST) variant protein comprising the amino acid sequence SEQ ID NO: 4 or SEQ ID NO: 6, wherein the contacting inhibits growth of the bacteria.

2. The method of claim 1, wherein the bacteria are *Staphylococcus aureus* (*S. aureus*) or methicillin-resistant *S. aureus* (MRSA).

3. The method of claim 1, wherein the LST variant protein is unglycosylated at the position corresponding to N125 of SEQ ID NO: 4.

4. The method of claim 1, wherein the LST variant protein is unglycosylated at the position corresponding to N125 of SEQ ID NO: 6.

5. An isolated unglycosylated lysostaphin variant protein comprising the amino acid sequence of SEQ ID NO: 4 or SEQ ID NO: 6.

6. The isolated unglycosylated lysostaphin variant protein of claim 5, wherein said protein comprises the amino acid sequence of SEQ ID NO: 4.

7. The isolated unglycosylated lysostaphin variant protein of claim 6, which is unglycosylated at the position corresponding to N125 of SEQ ID NO: 4.

8. The isolated unglycosylated lysostaphin variant protein of claim 5, wherein said protein comprises the amino acid sequence of SEQ ID NO: 6.

9. The isolated unglycosylated lysostaphin variant protein of claim 8, which is unglycosylated at the position corresponding to N125 of SEQ ID NO: 6.

* * * * *